(12) United States Patent
Dewey et al.

(10) Patent No.: US 7,850,717 B2
(45) Date of Patent: Dec. 14, 2010

(54) BONE ANCHORS HAVING TWO OR MORE PORTIONS EXHIBITING DIFFERENT PERFORMANCE CHARACTERISTICS AND METHOD OF FORMING THE SAME

(75) Inventors: Jonathan Dewey, Memphis, TN (US); Chris Patterson, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 606 days.

(21) Appl. No.: 11/365,565

(22) Filed: Mar. 1, 2006

(65) Prior Publication Data
US 2007/0233071 A1    Oct. 4, 2007

(51) Int. Cl.
*A61B 17/58* (2006.01)
*A61B 17/84* (2006.01)
*A61B 17/86* (2006.01)

(52) U.S. Cl. ............... 606/246; 606/300; 606/301; 606/302; 606/303; 606/304; 606/305; 606/306; 606/307; 606/308; 606/309; 606/315; 606/316; 606/317; 606/76; 606/77

(58) Field of Classification Search .............. 606/60, 606/61, 151, 312, 246, 264, 265, 279, 300–309, 606/322, 331, 76, 77; 623/17.11
See application file for complete search history.

(56) References Cited

U.S. PATENT DOCUMENTS

| | | | |
|---|---|---|---|
| 4,044,170 A | 8/1977 | Scharbach et al. | |
| 5,177,958 A * | 1/1993 | Clemens et al. | 60/293 |
| 5,360,448 A * | 11/1994 | Thramann | 606/60 |
| 5,395,371 A | 3/1995 | Miller et al. | |
| 5,643,263 A | 7/1997 | Simonson | |
| 5,810,821 A * | 9/1998 | Vandewalle | 606/65 |
| 5,824,247 A | 10/1998 | Tunc | |
| 5,947,967 A | 9/1999 | Barker | |
| 6,152,927 A | 11/2000 | Farris et al. | |
| 6,280,445 B1 | 8/2001 | Morrison et al. | |
| 6,740,086 B2 * | 5/2004 | Richelsoph | 606/60 |
| 6,783,527 B2 | 8/2004 | Drewry et al. | |
| 6,916,321 B2 * | 7/2005 | TenHuisen et al. | 606/312 |
| 7,235,079 B2 * | 6/2007 | Jensen et al. | 606/151 |
| 2005/0059972 A1 | 3/2005 | Biscup | |
| 2005/0240265 A1 * | 10/2005 | Kuiper et al. | 623/17.11 |

FOREIGN PATENT DOCUMENTS

| DE | 103 19 781 B3 | 8/2004 |
|---|---|---|
| GB | 2 073 024 A | 10/1981 |

* cited by examiner

*Primary Examiner*—Thomas C Barrett
*Assistant Examiner*—Sameh Boles (57) ABSTRACT

A bone anchor including a bone engaging element and an implant engaging element. The bone engaging element includes a first portion formed of a first material and a second portion formed of a second material and extending at least partially along a length of the first portion, and with the second portion of the bone engaging element positioned between the first portion and adjacent bone tissue when the bone engaging element is engaged with the bone to provide an interface with the adjacent bone tissue. In one embodiment, the first portion of the bone engaging element exhibits a first level of rigidity and the second portion exhibits a second level of rigidity less than the first level of rigidity. In another embodiment, the bone engaging element includes external threads, with the second portion of the bone engaging element defining at least a portion of the external threads.

38 Claims, 7 Drawing Sheets

BONE ANCHORS HAVING TWO OR MORE PORTIONS EXHIBITING DIFFERENT PERFORMANCE CHARACTERISTICS AND METHOD OF FORMING THE SAME

FIELD OF THE INVENTION

The present invention relates generally to the field of bone anchors, and more particularly relates to bone anchors having portions that exhibit different performance characteristics and methods of forming the same.

BACKGROUND

Various types of bone anchors are used to engage implants and other devices to bone. In the spinal field, bone anchors are commonly used to attach rods, plates, and other types of stabilization devices and implants to one or more vertebrae. Such bone anchors include, for example, screws, bolts, pins, nails, hooks, clamps, staples and other types of anchor devices configured to be anchored in or to bone.

Bone anchors are typically formed of a single, biocompatible material. As a result, various portions of the bone anchor exhibit similar performance characteristics. For example, bone anchors may be formed of rigid materials, such as titanium or stainless steel. While the use of such rigid materials provides sufficient strength and load carrying capabilities to avoid fractures or breakage, the interface between the bone anchor and the surrounding bone is non-flexible and unyielding, which tends to decrease bone growth around the bone anchor. Alternatively, bone anchors may be formed of semi-rigid materials, such as polymeric materials. While the use of such semi-rigid materials provides a flexible or yielding interface between the bone anchor and the surrounding bone, which tends to increase bone growth around the bone anchor, the strength and load carrying capabilities of the bone anchor are reduced, thereby increasing the risk of fracture or breakage.

Additionally, in some applications, it may be desirable to provide one or more portions of the bone anchor with different performance characteristics, such as, for example, varying strength, rigidity, porosity, absorption rate, degradation rate, etc. To achieve this result, bone anchors may include multiple pieces or components formed of different materials, with the pieces or components assembled together to form the bone anchor. However, bone anchors that are assembled from multiple pieces or components tend to result in increased fabrication and assembly costs. Additionally, the components of an assembled bone anchor are subject to loosening and/or separation.

Thus, there remains a need for improved bone anchors having portions that exhibit different performance characteristics and methods of forming the same. The present invention satisfies this need and provides other benefits and advantages in a novel and unobvious manner.

SUMMARY

The present invention relates generally to bone anchors having portions that exhibit different performance characteristics and methods of forming the same. While the actual nature of the invention covered herein can only be determined with reference to the claims appended hereto, certain forms of the invention that are characteristic of the preferred embodiments disclosed herein are described briefly as follows.

In one form of the present invention, a bone anchor is provided including a bone engaging element structured for engagement with bone, and an implant engaging element structured for coupling with an implant to anchor the implant to the bone. The bone engaging element includes a first portion formed of a first material and a second portion formed of a second material different from the first material and extending at least partially along a length of the first portion, and with the second portion of the bone engaging element positioned between the first portion and adjacent bone tissue when the bone engaging element is engaged with the bone to provide an interface with the adjacent bone tissue.

In another form of the present invention, a bone anchor is provided including a bone engaging element structured for engagement with bone, and an implant engaging element structured for coupling with an implant to anchor the implant to the bone. The bone engaging element includes a core portion exhibiting a first level of rigidity and a bone interface portion extending at least partially along a length of the core portion to provide a buffer between the core portion and adjacent bone tissue when the bone engaging element is engaged with the bone, and with the bone interface portion exhibiting a second level of rigidity less than the first level of rigidity exhibited by the core portion.

In another form of the present invention, a bone anchor is provided including a shank element having a length and defining external threads configured for engagement within an opening in bone, and an implant engaging element structured for coupling with an implant to anchor the implant to the bone. The shank element includes a core portion formed of a first a material and a bone interface portion formed of a second material that is less rigid than the first material, with the bone interface portion extending along a length of the core portion and about a periphery of the core portion, and with the bone interface portion defining at least a portion of the external threads of the shank element.

In another form of the present invention, a method is provided for forming a bone anchor, including providing a bone engaging element for anchoring to bone and an implant engaging element for coupling with an implant, forming a first portion of the bone engaging element from a first material with the first portion exhibiting a first level of rigidity, forming a second portion of the bone engaging element from a second material with the second portion exhibiting a second level of rigidity less than the first level of rigidity, the second portion of the bone engaging element extending along a length of the first portion and providing an interface between the first portion and adjacent bone when the bone engaging element is engaged to bone.

In another form of the present invention, a method is provided for forming a bone anchor, including providing a bone engaging element for anchoring to bone and an implant engaging element for coupling with an implant, forming a first portion of the bone engaging element from a first material, forming a second portion of the bone engaging element from a second material different from the first material, with the forming of the second portion of the bone engaging element comprising molding the second material about a periphery of the first portion and along a length of the first portion to provide an interface between the first portion and adjacent bone when the bone engaging element is engaged with the bone.

It is one object of the present invention to provide improved bone anchors having portions that exhibit different performance characteristics and methods of forming the same. Further objects, features, advantages, benefits, and aspects of the present invention will become apparent from the drawings and description contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 1:
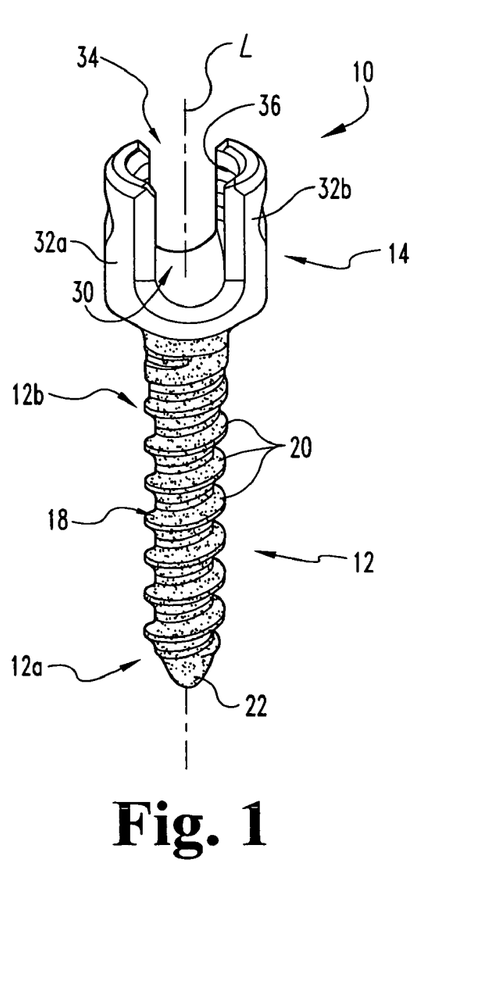
FIG. 1 is an elevational side view of a bone anchor according to one form of the present invention.
Figure 2:
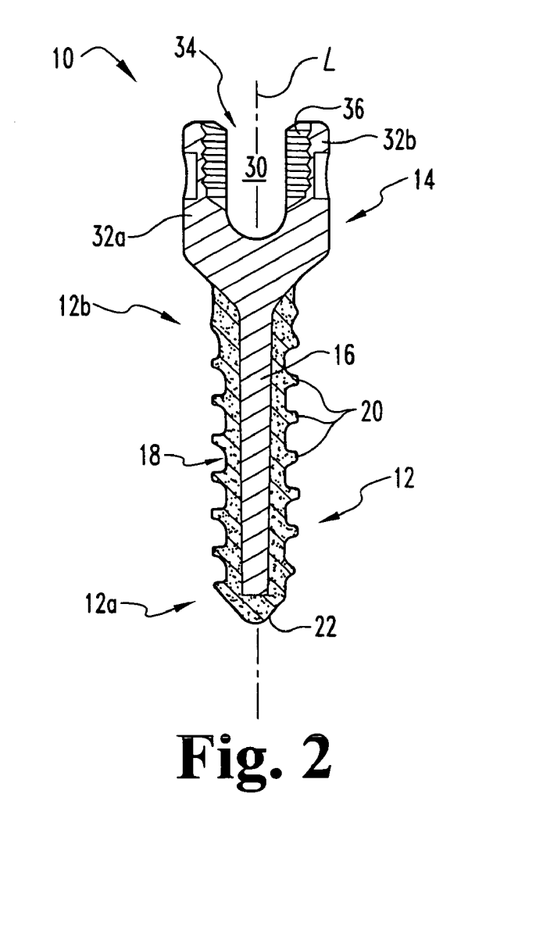
FIG. 2 is a cross sectional view of the bone anchor shown in FIG. 1.

Referring to FIGS. 1 and 2, shown therein is a bone anchor 10 according to one form of the present invention. The bone anchor 10 extends along a longitudinal axis L and generally includes a bone engaging portion 12 configured for anchoring in or to bone, and an implant engaging portion 14 configured for engaging an implant. The bone engaging portion 12 includes a distal region 12a and a proximal region 12b, with the implant engaging portion 14 extending from the proximal region 12b. In the illustrated embodiment, the bone anchor 10 is a bone screw, with the bone engaging portion 12 comprising an at least partially threaded shank configured for threading engagement within bone, and the implant engaging portion 14 comprising a screw head adapted for operative engagement with an implant. However, in other embodiments, the bone anchor 10 can take on other configurations, such as, for example, bolts, pins, nails, hooks, clamps, staples and other types of anchor devices capable of being anchored in or to bone. Further details regarding the bone engaging portion 12 and the implant engaging portion 14 of the bone anchor 10 will be discussed below.

In one embodiment of the invention, the bone engaging portion 12 of the bone anchor 10 is anchored within bone, and the implant engaging portion 14 is positioned outside of the bone. However, in other embodiments, the bone engaging portion 12 may be at least partially engaged to an exterior portion of the bone, such as is the case, for example, with bone anchors having a hook-type or clamp-type configuration. In other embodiments of the invention, the implant engaging portion 14 may be positioned partially within or entirely within the bone. The bone anchor 10 may be used to engage an orthopedic implant to bone, and more specifically a spinal implant to vertebral bone. However, it should be understood that the bone anchor 10 may be used in association with other types of implants outside of the orthopedic field or the spinal field. In the illustrated embodiments of the invention, the bone anchor 10 is configured to couple an elongate support member, such as, for example, a spinal rod or a spinal plate, to one or more vertebrae. However, it should be understood that the bone anchor 10 may also be used to couple other types of spinal implants or devices to bone, such as, for example, wires, cables, tethers, sutures, connectors, intervertebral implants, intravertebral implants, or other types of spinal implants or load carrying devices that would occur to one of ordinary skill in the art.

As indicated above, in one embodiment of the invention, the bone anchor 10 comprises a bone screw including an at least partially threaded shank portion 12 adapted for threading engagement within bone, and a screw head portion 14 adapted for operative engagement with an implant. In one aspect of the invention, the bone anchor 10 is formed of at least two different materials that exhibit different performance characteristics. In the illustrated embodiment, the bone engaging portion or threaded shank 12 is formed of two different materials. However, it should be understood that the bone engaging portion or threaded shank 12 may alternatively be formed of three of more different materials that exhibit different performance characteristics. Additionally, in other embodiments of the invention, the implant engaging portion or screw head 14 may be formed of a material different from that of the bone engaging portion 12, and/or may be formed of at least two different materials. In one embodiment of the invention, the materials from which the bone anchor 10 is formed exhibit different levels of rigidity, stiffness or strength. However, in other embodiments, the materials from which the bone anchor 10 is formed may be provided with other features that exhibit different performance characteristics, such as, for example, differing hardness, porosity, absorption or degradation rate, deformability, elasticity, fatigue resistance or load carrying capability.

As shown most clearly in FIG. 2, the threaded shank 12 includes in a core portion or inner layer 16 and a bone interface portion or outer layer 18 which provides a buffer between the core portion 16 and adjacent bone. In the illustrated embodiment, the core portion 16 extends generally along the longitudinal axis L and the bone interface portion extends peripherally about the core portion 16. However, it should be understood that the bone interface portion 18 need not necessarily extend entirely about the outer periphery of the core portion 16, but may instead extend partially about or may be positioned laterally adjacent the core portion 16. Additionally, in the illustrated embodiment, the bone interface portion 18 extends along substantially the entire length of the core portion 16, from the distal end 22 of the bone engaging portion 12 to a location proximate the implant engaging portion 14. However, as will be illustrated and described below, the bone interface portion 18 may alternatively extend along other axial regions of the core portion 16, and may extend along multiple axial regions of the core portion 16 in an intermittent or offset manner.

In one aspect of the invention, the core portion 16 is formed of a first material, and the bone interface portion 18 is formed of a second material that exhibits a higher level of rigidity or stiffness compared to the first material. Additionally, the core portion 16 may be formed of a first material, with the bone interface portion 18 formed of a second material that exhibits a higher level of flexibility compared to the first material. In one embodiment, the first and second materials from which the core portion 16 and the bone interfaces portion 18 are respectively formed comprise different materials. However, in other embodiments, the first and second materials may comprise the same material, but provided in a manner such that the core portion 16 and the bone interfaces portion 18 exhibit different degrees of rigidity, stiffness or strength.

In a further aspect of the invention, the first and second materials from which the core portion 16 and the bone interfaces portion 18 are respectively formed may exhibit other performance characteristics that differ from one another. For example, the core portion 16 may be formed of a first material, and the bone interface portion 18 may be formed of a second material that is softer compared to that of the first material to provide additional flexibility/pliability. Additionally, the core portion 16 may be formed of a first material, and the bone interface portion 18 may be formed of a second material that has a higher level of porosity compared to that of the first material to promote bone ingrowth or fusion. Further, the core portion 16 may be formed of a first material, and the bone interface portion 18 may be formed of a second material that exhibits a higher rate of absorption or degradation compared to that of the first material such that the bone interface portion 18 may be gradually replaced with bone over a period of time.

The materials used to form the core portion 16 and the bone interface portion 18 are preferably selected to be biologically and/or pharmacologically compatible and to exhibit minimal toxicity, both individually and when integrated together. In one embodiment, the core portion 16 is formed of a substantially rigid material, such as, for example, a metallic material including titanium, titanium alloys, stainless steel or stainless steel alloys. However, other metallic materials are also contemplated, including metal alloys such as chrome-cobalt alloys or shape-memory alloys. Additionally, the core portion 16 may be formed of other types of substantially rigid materials, such as, for example, ceramic materials, composite materials, certain polymer materials, or bone or bone substitute materials. In another embodiment, the bone interface portion 18 is formed of a semi-rigid or flexible/pliable material, such as, for example, a non-metallic material, including polymeric materials such as PEEK (polyetheretherketone) or a PEEK composite, shape-memory polymer materials, or other polymer materials or polymer composites. Additionally, the bone interface portion 18 may be formed of other types of semi-rigid or flexible/pliable materials, such as, for example, hydroxyapatite, composite materials, bone or bone substitute materials, or metallic materials which exhibit a relatively higher level of flexibility or elasticity compared to the material from which the core portion 16 is formed, including, for example, shape-memory alloy materials, titanium or titanium alloys, stainless steel or stainless steel alloys, aluminum or aluminum alloys, or chrome-cobalt alloys.

As should be appreciated, forming the core portion 16 of a first substantially rigid material provides sufficient strength and load carrying capabilities to the bone anchor 10 to reduce the risk of fracture or breakage. The implant engaging portion or screw head 14 is also preferably formed of a substantially rigid material to provide sufficient strength and load carrying capabilities to support the implant. As should also be appreciated, forming the bone interface portion 18 of a second material that is less rigid than the first material provides a more flexible/pliable interface or buffer layer between the bone engaging portion 12 and the surrounding bone, which in turn tends to increase bone growth around the bone engaging portion 12. Additionally, forming the bone interface portion 18 of a second material that is less rigid than the first material may also improve the load-sharing capabilities of the bone anchor 10 to more evenly and uniformly transfer loads between the bone engaging portion 12 and adjacent bone. In summary, forming the bone anchor 10 of at least two different materials minimizes the risk of fracture or breakage of the bone engaging portion 12, while at the same time facilitating bone growth about the bone engaging portion 12 and improving load transfer between the bone anchor and the adjacent bone. Accordingly, the bone anchor 10 is provided with a substantially rigid portion 16 that provides strength and rigidity, which is complemented by a less rigid portion 18 that provides a more flexible/pliable interface with adjacent bone to facilitate bone growth and improve load-sharing capabilities.

In the illustrated embodiment of the bone anchor 10, the bone engaging portion 12 includes bone anchoring elements 20 which are configured to engage bone, particularly vertebral bone, and more particularly cancellous vertebral bone. In one embodiment of the invention, the bone anchoring elements 20 are configured as a helical thread. However, it should be understood that other types and configuration of bone anchoring elements are also contemplated as falling with the scope of the present invention, including, for example, multiple thread-like elements which are formed by circumferentially, radially or axially interrupting a single thread, various types of raised projections extending about the outer periphery of the bone engaging portion 12 along a generally helical path, various types of grooves or recesses extending about the outer periphery of the bone engaging portion 12 along a generally helical path, ratchet elements that allow for relatively uninhibited insertion into bone in a first direction but which resist movement in an opposite second direction, spikes, annular or circular ridges, teeth, surface roughening, or any other type bone anchoring element that would occur to one of ordinary skill in the art.

In a specific embodiment, the bone engaging portion 12 includes a single lead thread 20 that has a uniform pitch and a uniform outer thread diameter and inner root diameter. However, in other embodiments, the bone engaging portion 12 may include a multi-lead thread, a variable thread pitch, a tapered outer thread diameter and/or a tapered inner root diameter. Additionally, the external threads 20 are illustrated as having relatively flat outer edges and include angled upper and lower thread surfaces that each extend in a direction oblique to the longitudinal axis L. However, other types and configurations of threads are also contemplated as falling within the scope of the present invention, including threads having pointed or rounded outer edges and/or thread configurations wherein one or both of the upper and lower thread surfaces are rounded or extend in a direction substantially normal to the longitudinal axis L.

In one embodiment of the invention, the implant engaging portion 14 is integral with the bone engaging portion 12 to define a unitary bone anchor 10. More specifically, the screw head 14 and the core portion 16 of the threaded shank 12 are formed as a single-piece, and the bone interface portion 18 is integrated with the core portion 16 in a manner which provides an integral, unitary bone anchor 10. However, in other embodiments, the screw head 14 and the core portion 16 may be formed as separate components and coupled to one another by any suitable attachment or connection technique, such as, for example, by welding, bonding, fusing, fastening, pinning, or by any other technique or process that would occur to one of ordinary skill in the art. Similarly, the bone interface portion 18 and the core portion 16 may be formed as separate components which are subsequently coupled or assembled together by any suitable attachment or connection technique.

In another aspect of the invention, the core portion 16 and the bone interface portion 18 are integrally formed to define a unitary element. In a specific embodiment, the bone interface portion 18 is molded with the core portion 16, such as, for example, by injection molding, overmolding, or other molding techniques or processes that would occur to one of ordinary skill in the art. It should be understood that such molding techniques and processes may be used in association with non-metallic materials such as polymers (via plastic injection molding), or in association with metallic materials (via metal injection molding). The core portion 16 may be treated or roughened to provide secure engagement between the bone interface portion 18 and the core portion 16. In other embodiments of the invention, the core portion 16 and the bone interface portion 18 may be integrated with one another via other suitable techniques or processes, such as, for example, by casting, melting, welding, bonding, fusing, plating, coating, spraying, forging, drawing, extruding, adhesion, fastening, pinning or by any other technique or process that would occur to one of ordinary skill in the art. In one embodiment, the core portion 16 and the bone interface portion 18 are integrated to define a unitary element, but are not joined at an atomic level. However, in other embodiments, the core portion 16 and the bone interface portion 18 may be joined at an atomic level to define a unitary, single-piece element.

In a further aspect of the invention, the core portion 16 does not define external threads. Instead, the external threads 20 are entirely defined by the bone interface portion 18. In one specific embodiment, the bone interface portion 18, including the external threads 20, may be formed about the core portion 16 via an injection molding technique, thereby eliminating the additional step of machining or cutting the external threads 20 into the bone interface portion 18. However, in another embodiment, the bone interface portion 18 may be formed about the core portion 16 via an overmolding technique, with the external threads 20 being formed into a solid overmolding via machining, cutting, rolling, deforming, or any other suitable technique or process for forming external threads. In alternative embodiments, full or partial threads may be formed along the core portion 16, with the bone interface portion 18 overlaid or applied over full or partial threads defined by the core portion 16.

In the illustrated embodiment of the bone anchor 10, the distal end 22 of the bone engaging portion 12 is tapered and defines a rounded tip. However, in another embodiment, the distal end 22 may define a pointed tip to facilitate penetration into bone. In still another embodiment, the distal end 22 may define a blunt or substantially flat end surface which may be provided with cutting elements, such as cutting teeth, to facilitate entry into bone. In a further embodiment, the distal region 12a of the bone engaging portion 12 may be provided with one or more cutting edges or flutes (not shown) to provide the bone anchor 10 with self-cutting or self-tapping capabilities. In yet another embodiment, the bone screw 10 may be provided with an axial passage or cannulation opening (not shown) extending either partially or entirely through the bone engaging portion 12, and may be further provided with transverse passages that communicate with the axial passage to define fenestration openings. The cannulation opening may be sized to receive an elongate member, such as a guide wire, to guide the bone anchor into a desired location adjacent the surgical site, and/or to guide other components into engagement with the bone anchor. Additionally, the cannulation and fenestration openings may be used to deliver material, such as, for example, bone cement, through the bone engaging portion 12 and into areas of the bone axially or laterally adjacent the distal region 12a or laterally adjacent other portions of the bone engaging portion 12.

In the illustrated embodiment of the bone anchor 10, the implant engaging portion or screw head 14 is configured for engagement with a spinal rod (not shown). In one specific embodiment, the screw head 14 defines a passage 30 sized to receive a spinal rod therein, with a fastener or setscrew (not shown) extending through the screw head 14 and into engagement with the spinal rod to capture and secure the spinal rod within the passage 30. In another specific embodiment, the screw head 14 includes a pair of spaced apart arms 32a, 32b defining an open end 34 which provide the passage 30 with a top-loading, U-shaped configuration, with the fastener or setscrew engaged with internal threads 36 extending along the spaced apart arms 32a, 32b. Further details regarding bone screws having configurations similar to the configuration of the bone anchor 10 are illustrated and described, for example, in U.S. Pat. No. 6,783,527 to Drewry et al., the contents of which are incorporated herein by reference.

In other embodiments of the invention, the screw head 14 may be configured as an unthreaded stem or shaft, with the spinal rod coupled to the screw head via a connector or coupling mechanism that includes a connector body defining a first passage for receiving the stem portion of the screw head, and a second passage for receiving the spinal rod. One or more fasteners or set screws may be threaded through corresponding openings in the connector body to secure the connector body to the stem portion of the bone screw and to the spinal rod. Further details regarding bone screw configurations and a connector or coupling mechanisms suitable for use in association with the present invention are illustrated and described, for example, in U.S. Pat. No. 5,643,263 to Simonson or U.S. Pat. No. 5,947,967 to Barker, the contents of each patent reference hereby incorporated herein by reference.

Figure 3:
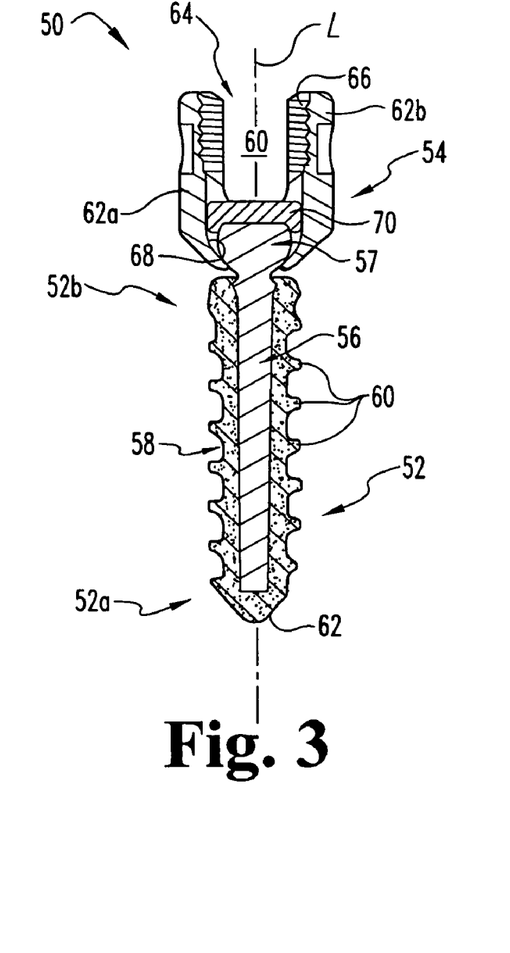
FIG. 3 is a cross sectional view of a bone anchor according to an alternative embodiment of the invention.

Referring to FIG. 3 shown therein is a bone anchor 50 according to another form of the present invention. The bone anchor 50 has a configuration similar to that of the bone anchor 10 illustrated and described above, extending along a longitudinal axis L and generally including a bone engaging portion 52 configured for anchoring in or to bone, and an implant engaging portion 54 configured for engaging an implant. The bone engaging portion 52 includes a distal region 52a and a proximal region 52b, with the implant engaging portion 54 extending from the proximal region 52b. In the illustrated embodiment, the bone anchor 50 is a bone screw, with the bone engaging portion 52 comprising a screw shank defining external threads 60 that are configured to engage bone, and with the implant engaging portion 54 comprising a screw head adapted for engagement with an implant. However, as indicated above, other types and configurations of bone anchors are also contemplated as falling within the scope of the present invention.

Unlike the bone anchor 10, which includes a bone engaging portion 12 that is fixed at a predetermined angle relative to the implant engaging portion 14, the bone anchor 50 is of the multi-axial type so as to allow relative pivotal or rotational movement between the bone engaging portion 52 and the implant engaging portion 54. More specifically, the bone engaging portion 52 is permitted to be selectively pivoted or rotated relative to the implant engaging portion 54 along multiple planes, or possibly along a single plane. Although the bone anchor 50 is illustrated and described as having a particular configuration, it should be understood that other types and configurations of multi-axial anchors are also contemplated for use in association with the present invention.

Similar to the bone anchor 10, the bone engaging portion 52 of the bone anchor 50 is formed of at least two different materials that exhibit different performance characteristics. In one embodiment, the bone engaging portion 52 includes a core portion or inner layer 56 and a bone interface portion or outer layer 58 which provides a buffer between the core portion 56 and adjacent bone. In one embodiment, the core portion 56 is formed of a first material, and the bone interface portion 58 is formed of a second material that is less rigid or stiff compared to the first material, and/or which exhibits other performance characteristics that differ from that of the first material. In the illustrated embodiment, the bone engaging portion 52 of the bone anchor 50 includes a rounded or spherical-shaped head 57 extending from the core portion 56, the function of which will be discussed below.

The bone engaging portion 52 includes a distal end 62 that is tapered and defines a rounded tip. However, in another embodiment, the distal end 62 may define a pointed tip to facilitate penetration into bone, or may define a blunt or substantially flat end surface which may be provided with cutting elements, such as cutting teeth, to facilitate entry into bone. The distal region 52a of the bone engaging portion 52 may also be provided with one or more cutting edges or flutes (not shown) to provide the bone anchor 50 with self-cutting or self-tapping capabilities. In yet another embodiment, the bone screw 50 may be provided with an axial passage or cannulation opening (not shown) extending either partially or entirely through the bone engaging portion 52, and may be further provided with transverse passages that communicate with the axial passage to define fenestration openings.

In the illustrated embodiment of the bone anchor 50, the implant engaging portion or screw head 54 is configured for engagement with a spinal rod (not shown). In one embodiment, the screw head 54 defines a passage 60 sized to receive a spinal rod therein, with a fastener or setscrew (not shown) extending through the screw head 54 and into engagement with the spinal rod to capture and secure the spinal rod within the passage 60. In another specific embodiment, the screw head 54 includes a pair of spaced apart arms 62a, 62b defining an open end 64 which provide the passage 60 with a top-loading, U-shaped configuration, and with a fastener or setscrew (not shown) engaged with the internal threads 66 along the spaced apart arms 62a, 62b to capture the spinal rod within the passage 60.

Furthermore, the screw head 54 includes a receptacle 68 that preferably has a rounded or spherical-shaped configuration so as to receive the spherical-shaped head 57 of the bone engaging portion 52 therein. The receptacle 68 and the spherical-shaped head 57 cooperate with one another to allow the bone engaging portion 52 to be selectively pivoted or rotated relative to the implant engaging portion 54 along multiple planes or about multiple axes. As should be appreciated, a locking member or crown 70 is positioned atop the spherical-shaped head 57 such that as the spinal rod (not shown) is displaced through the U-shaped passage 60 via a set screw (not shown) and into engagement with the crown 70, the crown 70 is compressed tightly against the spherical-shaped head 57 to lock the bone engaging portion 52 at a select angular orientation relative to the implant engaging portion 54. Further details regarding one type of multi-axial screw suitable for use in association with the present invention are illustrated and described, for example, in U.S. Pat. No. 5,797, 911 to Sherman et al., the contents of which are hereby incorporated herein by reference.

Figure 4:
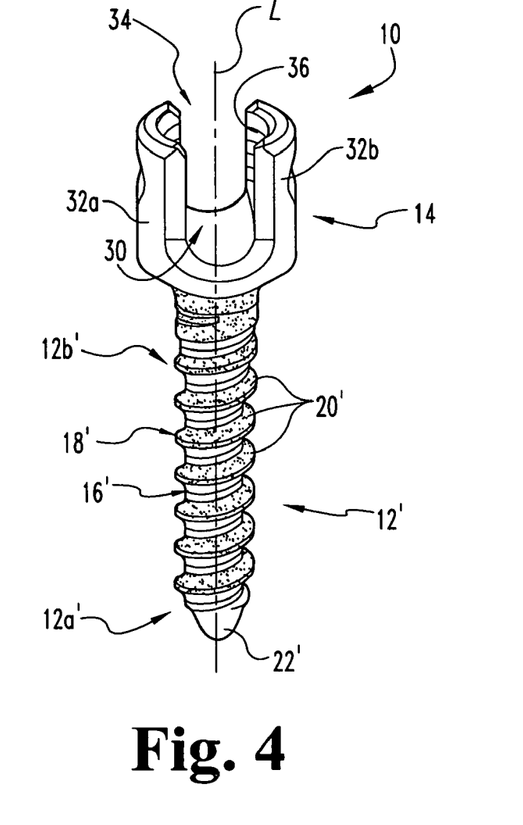
FIG. 4 is an elevational side view of a bone anchor according to another form of the present invention.
Figure 5:
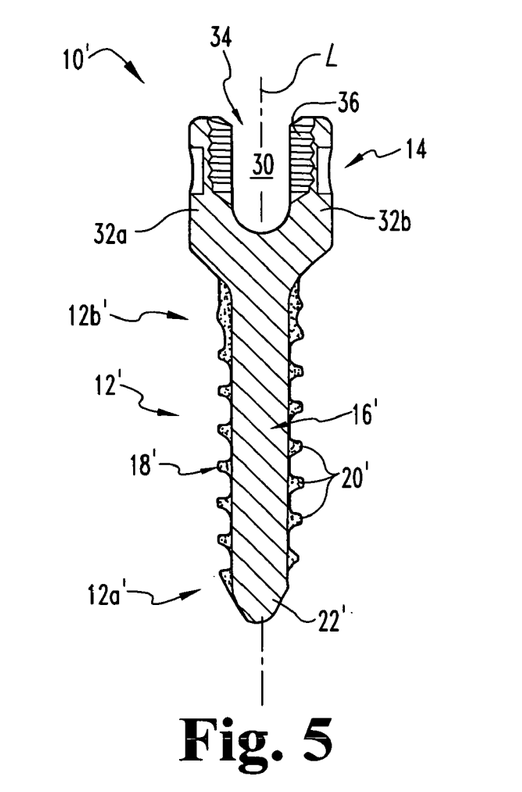
FIG. 5 is a cross sectional view of the bone anchor shown in FIG. 4.

Referring to FIGS. 4 and 5 shown therein is a bone anchor 10' according to another form of the present invention. The bone anchor 10' has a configuration similar to that of the bone anchor 10 illustrated and described above. Accordingly, common elements between the bone anchor 10 and the bone anchor 10' are indicated using the same reference numbers. The bone anchor 10' extends along a longitudinal axis L and generally includes a bone engaging portion 12' configured for anchoring in or to bone, and an implant engaging portion 14 configured for engaging an implant. The bone engaging portion 12' includes a distal region 12a' and a proximal region 12b', with the implant engaging portion 14 extending from the proximal region 12b'. In the illustrated embodiment, the bone anchor 10' is a bone screw, with the bone engaging portion 12' comprising a screw shank defining external threads 20' that are configured to engage bone, and with the implant engaging portion 14 comprising a screw head adapted for engagement with an implant. However, as indicated above, other types and configurations of bone anchors are also contemplated as falling within the scope of the present invention.

Similar to the bone anchor 10, the bone engaging portion 12' of the bone anchor 10' is formed of at least two different materials that exhibit different performance characteristics. In one embodiment, the bone engaging portion 12' includes a core portion or inner layer 16' and a bone interface portion or outer layer 18' which provides a buffer between the core portion 16' and adjacent bone. Like the bone anchor 10, the core portion 16' is formed of a first material, and the bone interface portion 18' is formed of a second material that is less rigid or stiff compared to the first material and/or which exhibits other performance characteristics that differ from that of the first material. However, unlike the bone anchor 10, where the bone interface portion 18 has a depth which extends inwardly beyond the inner root diameter of the external threads 20, the bone interface portion 18' of the bone anchor 10' has a depth which extends to a point just short of the inner root diameter of the external threads 20'. In other words, while the external threads 20' are defined almost entirely by the bone interface portion 18', the inner portion of the screw shank 12' starting at the inner root diameter of the threads 20' is defined by the core portion 16'. In the illustrated embodiment of the bone anchor 10', the distal end 22' of the bone engaging portion 12' is defined by the core portion 16'. However, in other embodiments, the bone interface portion 18' may extend either partially or entirely about the distal end 22'.

In an alternative embodiment of the invention, the bone anchor 10' may be configured such that the core portion 16' extends outwardly beyond the inner root diameter of the threads 20' so as to define a base portion of the threads 20', with the outer portion of the threads 20' being defined by the bone interface portion 18'. In a further embodiment of the invention, the bone anchor 10' may be configured such that the projecting region of the threads 20' is defined by the core portion 16', while the recessed region of the threads 20' is defined by the bone interface portion 18'. In other words, the bone anchor 10' may be configured such the outer end portions or tips of the threads 20' are defined by the core portion 16', while the inner grooves or troughs of the threads 20' (including the inner root diameter) are defined by the bone interface portion 18'. Other embodiments of the invention are also contemplated where various portions of the external threads 20' may be defined by the core portion 16', while the remaining portions of the threads 20' are defined by the bone interface portion 18'.

Figure 6:
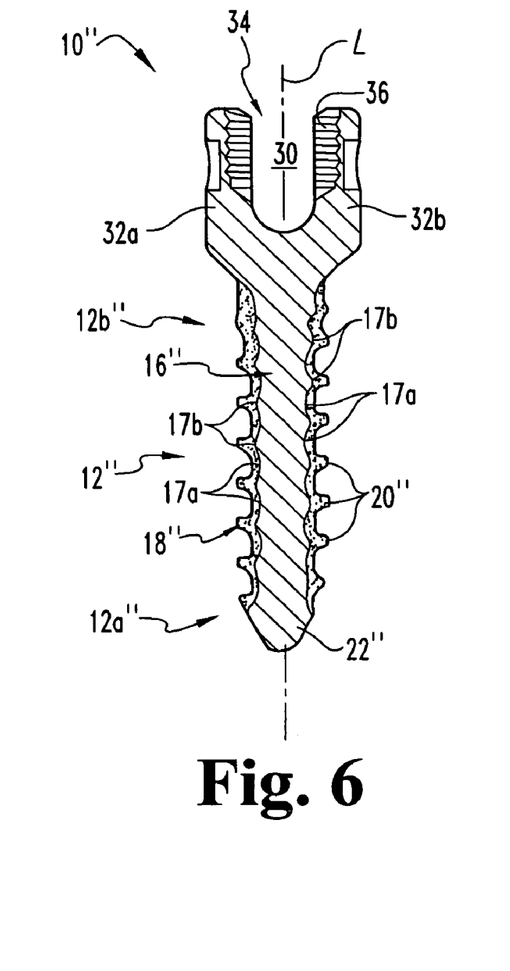
FIG. 6 is a cross sectional view of a bone anchor according to an alternative embodiment of the invention.

Referring to FIG. 6 shown therein is a bone anchor 10" according to yet another form of the present invention. The bone anchor 10" has a configuration similar to that of the bone anchors 10 illustrated and described above. Accordingly, common elements between the bone anchor 10 and the bone anchor 10" are indicated using the same reference numbers. The bone anchor 10" extends along a longitudinal axis L and generally includes a bone engaging portion 12" configured for anchoring in or to bone, and an implant engaging portion 14 configured for engaging an implant. The bone engaging portion 12" includes a distal region 12a" and a proximal region 12b", with the implant engaging portion 14 extending from the proximal region 12b". In the illustrated embodiment, the bone anchor 10" is a bone screw, with the bone engaging portion 12" comprising a screw shank defining external threads 20" that are configured to engage bone, and with the implant engaging portion 14 comprising a screw head adapted for engagement with an implant. However, as indicated above, other types and configurations of bone anchors are also contemplated as falling within the scope of the present invention.

Similar to the bone anchor 10, the bone engaging portion 12" of the bone anchor 10" is formed of at least two different materials that exhibit different performance characteristics. In one embodiment, the bone engaging portion 12" includes a core portion or inner layer 16" and a bone interface portion or outer layer 18" which provides a buffer between the core portion 16" and adjacent bone. Like the bone anchor 10, the core portion 16" is formed of a first material, and the bone interface portion 18" is formed of a second material that is less rigid or stiff compared to the first material and/or which exhibits other performance characteristics that differ from that of the first material. However, unlike the bone anchor 10, where the core portion 16 is configured to have a substantially smooth outer surface, the core portion 16" of the bone anchor 10" defines a recess or trough 17a that extends about the core portion 16" along a generally helical path, with the remainder of the outer periphery of the core portion 16" being defined by a helical ridge or plateau 17b. Accordingly, the core portion 16' is provided with an outer profile that substantially corresponds to the outer profile of the external threads 20" defined by the bone interface portion 18". In the illustrated embodiment of the bone anchor 10", the helical recess 17a extending about the core portion 16" is generally aligned with the helical recess defined by the threads 20", and with the helical ridge 17b generally aligned with the outer helical portion of the threads 20". However, in other embodiments, the helical recess 17a extending about the core portion 16" may be axially offset relative to the helical recess defined by the threads 20". For example, the helical recess 17a may be generally aligned with the outer helical portion of the threads 20". Other suitable arrangements are also contemplated. Additionally, in the illustrated embodiment of the bone anchor 10", the distal end 22" of the bone engaging portion 12" is defined by the core portion 16". However, in other embodiments, the bone interface portion 18" may extend either partially or entirely about the distal end 22".

Figure 7:
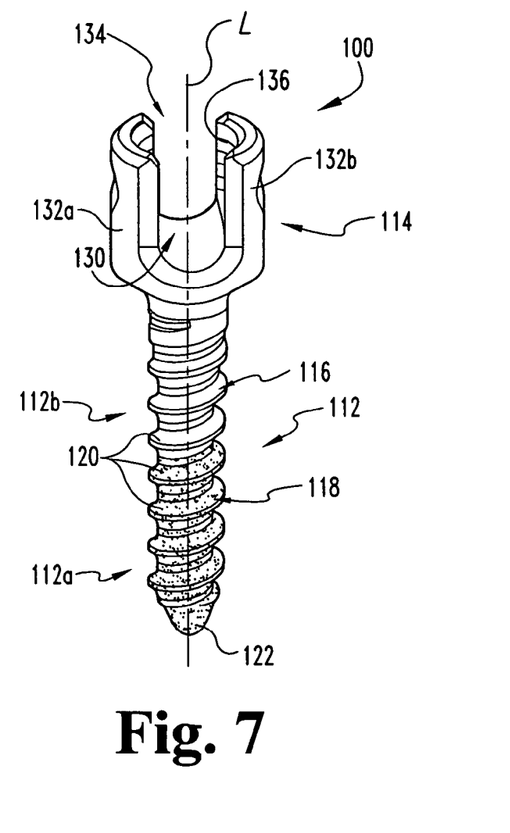
FIG. 7 is an elevational side view of a bone anchor according to another form of the present invention.
Figure 8:
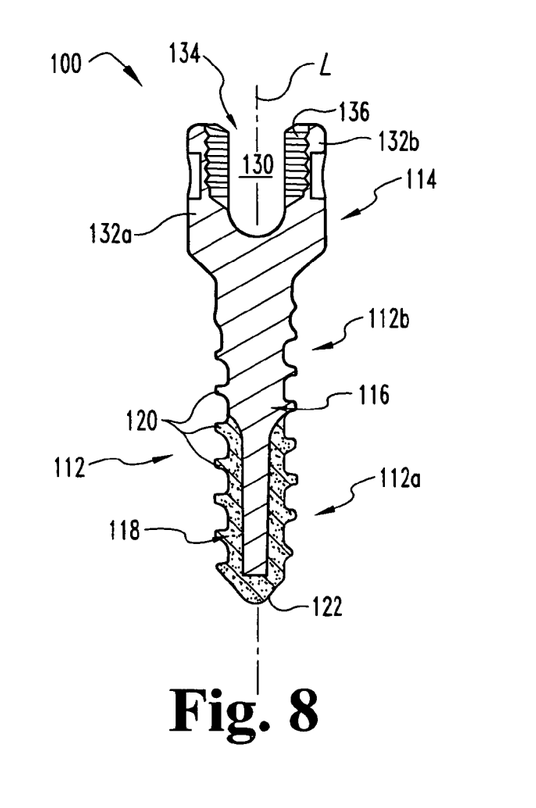
FIG. 8 is a cross sectional view of the bone anchor shown in FIG. 7.

Referring to FIGS. 7 and 8 shown therein is a bone anchor 100 according to another form of the present invention. The bone anchor 100 has a configuration similar to that of the bone anchor 10 illustrated and described above. Specifically, the bone anchor 100 extends along a longitudinal axis L and generally includes a bone engaging portion 112 configured for anchoring in or to bone, and an implant engaging portion 114 configured for engaging an implant. The bone engaging portion 112 includes a distal region 112a and a proximal region 112b, with the implant engaging portion 114 extending from the proximal region 112b. In the illustrated embodiment, the bone anchor 100 is a bone screw, with the bone engaging portion 112 comprising a screw shank defining external threads 120 that are configured to engage bone, and with the implant engaging portion 114 comprising a screw head adapted for engagement with an implant. However, as indicated above, other types and configurations of bone anchors are also contemplated as falling within the scope of the present invention.

Similar to the bone anchor 10, the bone engaging portion 112 of the bone anchor 100 is formed of at least two different materials that exhibit different performance characteristics. In one embodiment, the bone engaging portion 112 includes a core portion or inner layer 116 and a bone interface portion or outer layer 118 which provides a buffer between the core portion 116 and adjacent bone. Like the bone anchor 10, the core portion 116 is formed of a first material, and the bone interface portion 118 is formed of a second material that is less rigid or stiff compared to the first material and/or which exhibits other performance characteristics that differ from that of the first material. However, unlike the bone anchor 10 where the bone interface portion 18 extends along substantially the entire length of the core portion 16, the bone interface portion 118 extends along only a portion of the length of the core portion 116. Specifically, the bone interface portion 118 extends along the distal region 112a of the bone engaging portion 112, with the proximal region 112b defined by the core portion 116 interfacing directly with the bone. In the illustrated embodiment of the bone anchor 100, the bone interface portion 118 extends along the entire distal region 112a of the bone engaging portion 112, including the distal end 122.

Alternatively, the bone interface portion 118 may extend along other axial regions of the bone engaging portion 112. In other embodiments, the bone interface portion 118 may extend along two or more axial regions of the bone engaging portion 112, including configurations where the bone interface portion 118 extends along the distal region 112a and the proximal region 112b of the bone engaging portion 112, with an intermediate region of the bone engaging portion 112 defined by the core portion 116 interfacing directly with the bone. In still other embodiments, the bone interface portion 118 may extend along a central region of the bone engaging portion 112, with distal and proximal regions 112a, 112b of the bone engaging portion 112 defined by the core portion 116 interfacing directly with the bone.

As indicated above with regard to the bone anchor 10, forming the core portion 116 of a first substantially rigid material provides sufficient strength and load carrying capabilities to the bone anchor 100, and particularly the bone engaging portion 112, to reduce the risk of fracture or breakage. The implant engaging portion or screw head 114 is also preferably formed of a substantially rigid material to provide sufficient strength and load carrying capabilities to support the implant. As also indicated above, forming the bone interface portion 118 of a second material that is less rigid than the first material provides a more flexible/pliable interface or buffer layer between the bone engaging portion 112 and the surrounding bone, which in turn tends to increase bone growth around the bone engaging portion 112, and which may also increase the load-sharing capabilities of the bone anchor 100 to more evenly or uniformly transfer loads between the bone engaging portion 112 and adjacent bone.

Additionally, as should be appreciated, the external threads 120 along the proximal region 112b of the bone engaging portion 112 (adjacent the screw head 114) are defined by the substantially rigid core portion 116, whereas the external threads 120 along the distal region 112a are defined by the less rigid and more flexible/pliable bone interface portion 118. Such a configuration provides rigid threads 120 adjacent the location where the bone engaging portion 112 exits the bone, thereby providing a more solid and stable fit with the surrounding bone at this location, which in turn tends to reduce the tendency of the bone engaging portion 112 to loosen and back out from the bone. Additionally, providing rigid threads 120 adjacent the location where the bone engaging portion 112 exits the bone provides additional strength in the region of the bone anchor 100 which typically experiences relatively high lateral or torsional loading and stresses, thereby tending to reduce the risks associated with fracture or breakage.

In the illustrated embodiment of the bone anchor 100, the screw head 114 is configured for engagement with a spinal rod (not shown). Specifically, the screw head 114 defines a passage 130 sized to receive a spinal rod therein, and includes a pair of spaced apart arms 132a, 132b defining an open end 134 which provide the passage 130 with a top-loading, U-shaped configuration, and with a fastener or setscrew (not shown) threadingly engaged with internal threads 136 formed along the spaced apart arms 132a, 132b and engaging the spinal rod to capture and secure the spinal rod within the passage 130. However, it should be understood that other configurations of the implant engaging portion 114 are also contemplated as falling within the scope of the present invention. In the illustrated embodiment of the bone anchor 100, the distal end 122 of the bone engaging portion 112 is tapered and defines a rounded tip. However, in other embodiments, the distal end 122 may define a pointed tip to facilitate penetration into bone, or may define a blunt or substantially flat end surface which may be provided with cutting elements, such as cutting teeth, to facilitate entry into bone. In other embodiment, the distal region 112a of the bone engaging portion 112 may be provided with one or more cutting edges or flutes (not shown) to provide the bone anchor 100 with self-cutting or self-tapping capabilities, and/or may be provided with a full or partial cannulation opening and transverse fenestration openings.

Figure 9:
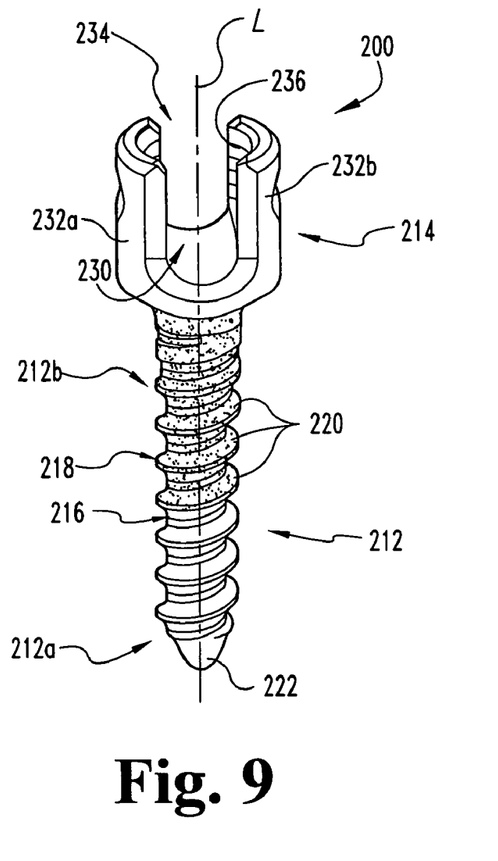
FIG. 9 is an elevational side view of a bone anchor according to another form of the present invention.
Figure 10:
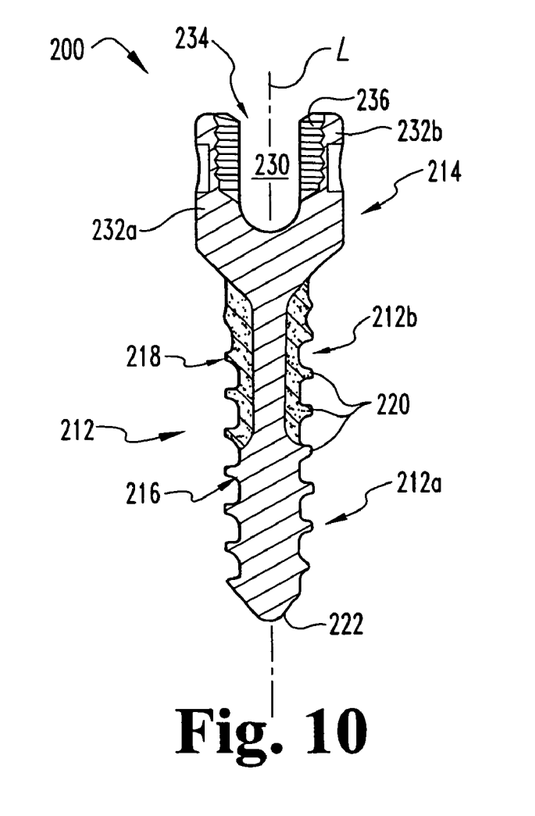
FIG. 10 is a cross sectional view of the bone anchor shown in FIG. 9.

Referring to FIGS. 9 and 10, shown therein is a bone anchor 200 according to another form of the present invention. The bone anchor 200 has a configuration similar to that of the bone anchors 10 and 100 illustrated and described above, extending along a longitudinal axis L and generally including a bone engaging portion 212 and an implant engaging portion 214, with the bone engaging portion 212 having a distal region 212a and a proximal region 212b, and with the implant engaging portion 214 extending from the proximal region 212b. In the illustrated embodiment, the bone anchor 200 is a bone screw, with the bone engaging portion 212 comprising a screw shank defining external threads 220 that are configured to engage bone, and with the implant engaging portion 214 comprising a screw head adapted for engagement with an implant. However, as indicated above, other types and configurations of bone anchors are also contemplated as falling within the scope of the present invention.

Similar to the bone anchors 10 and 100, the bone engaging portion 212 of the bone anchor 200 is formed of at least two different materials that exhibit different performance characteristics. In one embodiment, the bone engaging portion 212 includes a core portion or inner layer 216 and a bone interface portion or outer layer 218 which provides a buffer between the core portion 216 and adjacent bone, with the core portion 216 formed of a first material, and the bone interface portion 218 formed of a second material that is less rigid or stiff compared to the first material and/or which exhibits other performance characteristics that differ from that of the first material. However, unlike the bone anchors 10 and 100, the bone interface portion 218 extends along only the proximal region 212b of the bone engaging portion 212, with the distal region 212a defined by the core portion 216 interfacing directly with the bone. In one embodiment, the bone interface portion 218 extends along the entire proximal region 212b of the bone engaging portion to a location proximate the implant engaging portion 214.

As indicated above with regard to the bone anchors 10 and 100, forming the core portion 216 of a first substantially rigid material provides sufficient strength and load carrying capabilities to the bone anchor 200, and particularly the bone engaging portion 212, to reduce the risk of fracture or breakage. The implant engaging portion or screw head 214 is also preferably formed of a substantially rigid material to provide sufficient strength and load carrying capabilities to support the implant. As also indicated above, forming the bone interface portion 218 of a second material that is less rigid than the first material provides a more flexible/pliable interface or buffer layer between the bone engaging portion 212 and the surrounding bone, which in turn tends to increase bone growth around the bone engaging portion 212, and which may also increase the load-sharing capabilities of the bone anchor 200 to more evenly or uniformly transfer loads between the bone engaging portion 212 and adjacent bone.

Additionally, as should be appreciated, the external threads 220 along the distal region 212a of the bone engaging portion 212 are defined by the substantially rigid core portion 216, whereas the external threads 220 along the proximal region 212b are defined by the less rigid and more flexible/pliable bone interface portion 218. Such a configuration provides additional strength and rigidity adjacent the distal end portion 222 to withstand relatively high loads and stresses which may be realized during initial penetration of the bone engaging portion 212 into bone, and particularly the outer cortical bone layer which is relatively tougher/harder than the inner cancellous bone, thereby tending to reduce the risks associated with fracture or breakage. This configuration is particularly beneficial in embodiments where the bone anchor 200 is provided with self-cutting or self-tapping capabilities, including embodiments wherein one or more cutting edges or flutes (not shown) are formed on the bone engaging portion 212 adjacent the distal end 222. As should be appreciated, the forces and stresses exerted onto the distal end 222 of the bone engaging portion 212 can be particularly high during the formation of the opening in bone and/or during the cutting of internal threads in bone.

In the illustrated embodiment of the bone anchor 200, the screw head 214 is configured for engagement with a spinal rod (not shown). Specifically, the screw head 214 defines a passage 230 sized to receive a spinal rod therein, and includes a pair of spaced apart arms 232a, 232b defining an open end 234 which provide the passage 230 with a top-loading, U-shaped configuration, and with a fastener or setscrew (not shown) threadingly engaged with internal threads 236 formed along the spaced apart arms 232a, 232b and engaging the spinal rod to capture and secure the spinal rod within the passage 230. However, it should be understood that other configurations of the implant engaging portion 214 are also contemplated as falling within the scope of the present invention. In the illustrated embodiment of the bone anchor 200, the distal end 222 of the bone engaging portion 212 is tapered and defines a rounded tip. However, in other embodiments, the distal end 222 may define a pointed tip to facilitate penetration into bone, or may define a blunt or substantially flat end surface which may be provided with cutting elements, such as cutting teeth, to facilitate entry into bone. In other embodiment, the distal region 212a of the bone engaging portion 212 may be provided with a full or partial cannulation opening and transverse fenestration openings.

Figure 11:
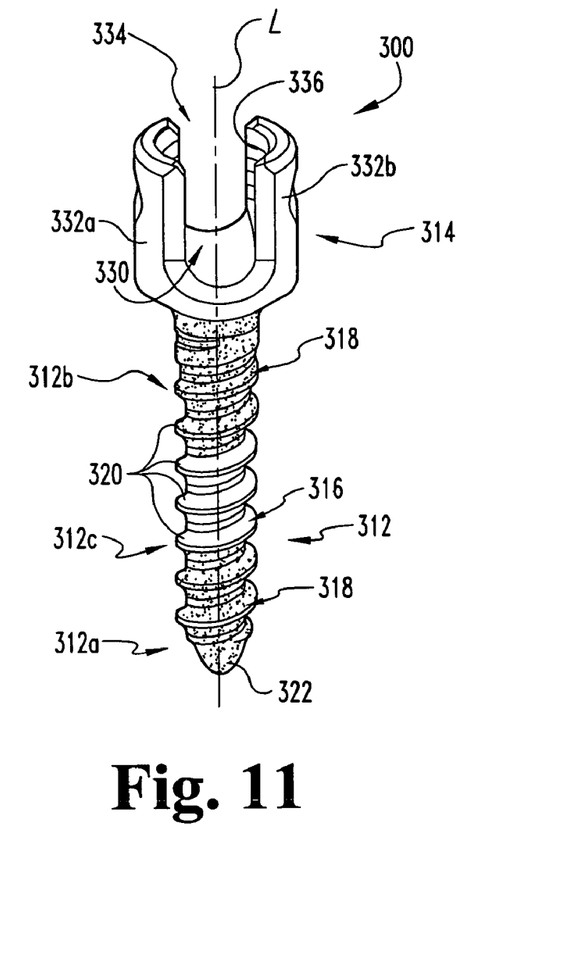
FIG. 11 is an elevational side view of a bone anchor according to another form of the present invention.
Figure 12:
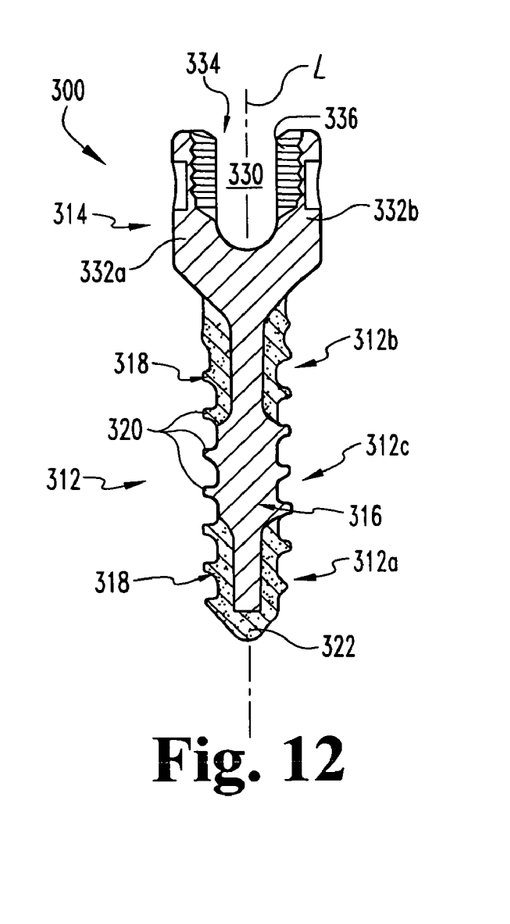
FIG. 12 is a cross sectional view of the bone anchor shown in FIG. 11.

Referring to FIGS. 11 and 12, shown therein is a bone anchor 300 according to another form of the present invention. The bone anchor 300 has a configuration similar to that of the bone anchors 100 and 200 illustrated and described above, extending along a longitudinal axis L and generally including a bone engaging portion 312 and an implant engaging portion 314, with the bone engaging portion 312 having a distal region 312a, a proximal region 312b and a intermediate or central region 312c, and with the implant engaging portion 314 extending from the proximal region 312b. In the illustrated embodiment, the bone anchor 300 is a bone screw, with the bone engaging portion 312 comprising a screw shank defining external threads 320 that are configured to engage bone, and with the implant engaging portion 314 comprising a screw head adapted for engagement with an implant. However, as indicated above, other types and configurations of bone anchors are also contemplated as falling within the scope of the present invention.

Similar to the bone anchors 100 and 200, the bone engaging portion 312 of the bone anchor 300 is formed of at least two different materials that exhibit different performance characteristics. In one embodiment, the bone engaging portion 312 includes a core portion or inner layer 316 and a bone interface portion or outer layer 318 which provides a buffer between the core portion 316 and adjacent bone, with the core portion 316 formed of a first material, and the bone interface portion 318 formed of a second material that is less rigid or stiff compared to the first material and/or which exhibits other performance characteristics that differ from that of the first material.

However, unlike the bone anchors 100 and 200, the bone interface portion 318 extends along the distal and proximal regions 312a and 312b of the bone engaging portion 312, with the intermediate or central region 312c defined by the core portion 316 interfacing directly with the bone. In one embodiment, the bone interface portion 318 extends along the entire distal region 312a of the bone engaging portion, including the distal end 322, and along the entire proximal region 312b of the bone engaging portion to a location proximate the implant engaging portion 314. In an alternative embodiment of the invention, the bone interface portion 318 may be provided along the intermediate or central region 312c of the bone engaging portion, with the distal and proximal regions 312a and 312b being defined by the core portion 316 such that the distal and proximal regions 312a and 312b interface directly with bone.

It should be understood that other embodiments of the invention are also contemplated wherein one, two or three or more axial regions of the bone engaging portion 312 may be defined by the bone interface portion 318, and with one, two or three or more axial regions of the bone engaging portion 312 being defined by the core portion 316 which interface directly with bone. Additionally, in one embodiment of the invention, axial regions of the bone engaging portion 312 defined by the bone interface portion 318 may be provided in an alternating manner relative to axial regions defined by the core portion 316. Furthermore, it should also be understood that other embodiments of the invention are also contemplated wherein one, two or three or more longitudinally-extending regions of the bone engaging portion 312 may be defined by the bone interface portion 318, with one, two or three or more longitudinally-extending regions of the bone engaging portion 312 being defined by the core portion 316 which interface directly with bone. The longitudinally-extending regions defined by the bone interface portion 318 may be provided in an alternating manner relative to the longitudinally-extending regions defined by the core portion 316.

As indicated above with regard to the bone anchors 100 and 200, forming the core portion 316 of a first substantially rigid material provides sufficient strength and load carrying capabilities to the bone anchor 300, and particularly the bone engaging portion 312, to reduce the risk of fracture or breakage. The implant engaging portion or screw head 314 is also preferably formed of a substantially rigid material to provide sufficient strength and load carrying capabilities to support the implant. As also indicated above, forming the bone interface portion 318 of a second material that is less rigid than the first material provides a more flexible/pliable interface or buffer layer between the bone engaging portion 312 and the surrounding bone, which in turn tends to increase bone growth around the bone engaging portion 312, and which may also increase the load-sharing capabilities of the bone anchor 300 to more evenly or uniformly transfer loads between the bone engaging portion 312 and adjacent bone. In one embodiment of the invention, the axial regions of the bone engaging portion 312 defining the bone interface portion 318 (e.g., the distal and proximal regions 312a, 312b) are formed of the same material. However, in other embodiments of the invention, the axial regions of the bone engaging portion 312 defining the bone interface portion 318 may be formed of different materials.

In the illustrated embodiment of the bone anchor 300, the screw head 314 is configured for engagement with a spinal rod (not shown). Specifically, the screw head 314 defines a passage 330 sized to receive a spinal rod therein, and includes a pair of spaced apart arms 332a, 332b defining an open end 334 which provide the passage 330 with a top-loading, U-shaped configuration, and with a fastener or setscrew (not shown) threadingly engaged with internal threads 336 formed along the spaced apart arms 332a, 332b and engaging the spinal rod to capture and secure the spinal rod within the passage 330. However, it should be understood that other configurations of the implant engaging portion 314 are also contemplated as falling within the scope of the present invention. In the illustrated embodiment of the bone anchor 300, the distal end 322 of the bone engaging portion 312 is tapered and defines a rounded tip. However, in other embodiments, the distal end 322 may define a pointed tip to facilitate penetration into bone, or may define a blunt or substantially flat end surface which may be provided with cutting elements, such as cutting teeth, to facilitate entry into bone. In other embodiment, the distal region 312a of the bone engaging portion 312 may be provided with a full or partial cannulation opening and transverse fenestration openings.

Figure 13:
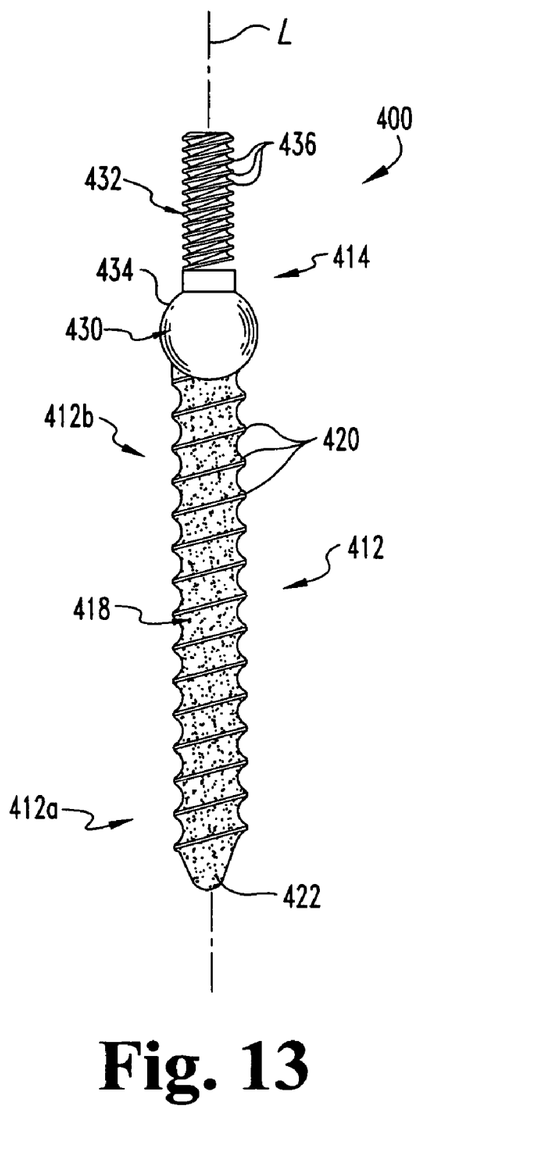
FIG. 13 is an elevational side view of a bone anchor according to another form of the present invention.
Figure 14:
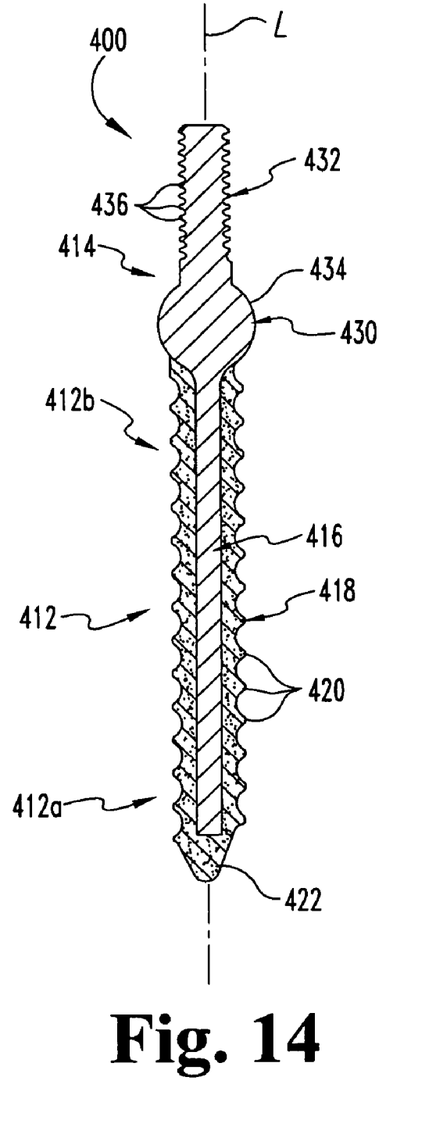
FIG. 14 is a cross sectional view of the bone anchor shown in FIG. 13.

Referring to FIGS. 13 and 14, shown therein is a bone anchor 400 according to another form of the present invention. The bone anchor 400 extends along a longitudinal axis L and generally includes a bone engaging portion 412 configured for anchoring in or to bone, and an implant engaging portion 414 configured for engaging an implant. In the illustrated embodiment, the bone anchor 400 is a bone screw, with the bone engaging portion 412 comprising a threaded shank and the implant engaging portion 414 comprising a screw head adapted for engagement with an implant. However, in other embodiments, the bone anchor 400 can take on other configurations, such as, for example, bolts, pins, nails, hooks, clamps, staples and other types of anchor devices capable of being anchored to bone.

The bone engaging portion 412 is configured similar to the bone engaging portion 12 of the bone anchor 10 illustrated and described above, and includes a distal region 412a and a proximal region 412b, with the implant engaging portion 414 extending from the proximal region 412b. Additionally, similar to the bone anchor 10, the bone engaging portion 412 of the bone anchor 400 is formed of at least two different materials that exhibit different performance characteristics. In one embodiment, the bone engaging portion 412 includes a core portion or inner layer 416 and a bone interface portion or outer layer 418 which provides a buffer between the core portion 416 and adjacent bone. The core portion 416 is formed of a first material, and the bone interface portion 418 is formed of a second material that is less rigid or stiff compared to the first material and/or which exhibits other performance characteristics that differ from that of the first material. Additionally, like the bone anchor 10, the bone interface portion 418 extends along substantially the entire length of the core portion 416, from the distal end 422 to a location proximate the implant engaging portion 414. However, as illustrated and described above, the bone interface portion 418 may alternatively extend along other axial regions of the core portion 416, and may extend along multiple axial regions of the core portion 416 in an offset or intermittent manner.

As indicated above with regard to the bone anchor 10, forming the core portion 416 of a first substantially rigid material provides sufficient strength and load carrying capabilities to the bone anchor 400, and particularly the bone engaging portion 412, to reduce the risk of fracture or breakage. The implant engaging portion or screw head 414 is also preferably formed of a substantially rigid material to provide sufficient strength and load carrying capabilities to support the implant. As also indicated above, forming the bone interface portion 418 of a second material that is less rigid than the first material provides a more flexible/pliable interface or buffer layer between the bone engaging portion 412 and the surrounding bone, which in turn tends to increase bone growth around the bone engaging portion 412, and which may also increase the load-sharing capabilities of the bone anchor 400 to more evenly or uniformly transfer loads between the bone engaging portion 412 and adjacent bone. As should be appreciated, forming the bone anchor 400 of at least two different materials in the manner described above minimizes the risk of fracture or breakage of the bone engaging portion 412, while also facilitating bone growth about the bone engaging portion 412 and transferring of loads from the bone engaging portion 412 to adjacent bone. In summary, the bone anchor 400 includes a substantially rigid portion 416 that provides sufficient strength and rigidity, and is complemented by a less rigid portion 418 that provides a more flexible/pliable interface with adjacent bone to facilitate bone growth and load-sharing capabilities.

In the illustrated embodiment of the bone anchor 400, the bone engaging portion 412 includes external threads 420 that are configured to engage bone, particularly vertebral bone, and more particularly cancellous vertebral bone. Although the bone anchor 400 is illustrated as including a particular type and configuration of external threads 420, it should be understood that other types and configurations of threads are also contemplated for use in association with the bone anchor 400. In one embodiment, the implant engaging portion 414 is integral with the bone engaging portion 412 to define a unitary bone anchor 400. More specifically, the screw head 414 and the core portion 416 of the threaded shank 412 are formed as a single-piece, and the bone interface portion 418 is integrated with the core portion 416 to provide a unitary bone anchor 400. However, other configurations are also contemplated. In a specific embodiment, the bone interface portion 418 is molded with the core portion 416, such as, for example, by injection molding, overmolding, or other molding techniques or processes that would occur to one of ordinary skill in the art. However, in other embodiments, the core portion 416 and the bone interface portion 418 may be integrated with one another via other suitable techniques or processes, such as, for example, by casting, melting, welding, bonding, fusing, plating, coating, spraying, forging, drawing, extruding, adhesion, fastening, pinning or by any other technique or process that would occur to one of ordinary skill in the art.

In a further embodiment of the invention, the core portion 416 does not define external threads. Instead, the external threads 420 are entirely defined by the bone interface portion 418. In one specific embodiment, the bone interface portion 418, including the external threads 420, may be formed about the core portion 416 via an injection molding technique, thereby eliminating the additional step of machining or cutting the external threads 420 into the bone interface portion 418. However, in another embodiment, the bone interface portion 418 may be formed about the core portion 416 via an overmolding technique, with the external threads 420 being formed into a solid overmolding via machining, cutting or any other suitable technique or process for forming external threads. In alternative embodiments, full or partial threads may be formed along the core portion 416, with the bone interface portion 418 overlaid or applied over the full or partial threads of the core portion 416.

In the illustrated embodiment of the bone anchor 400, the distal end 422 of the bone engaging portion 412 is tapered and defines a rounded tip. However, in another embodiment, the distal end 422 may define a pointed tip to facilitate penetration into bone. In still another embodiment, the distal end 422 may define a blunt or substantially flat end surface which may be provided with cutting elements, such as cutting teeth, to facilitate entry into bone. In a further embodiment, the distal region 412a of the bone engaging portion 12 may be provided with one or more cutting edges or flutes (not shown) to provide the bone anchor 400 with self-cutting or self-tapping capabilities. In yet another embodiment, the bone screw 10 may be provided with an axial passage or cannulation opening (not shown) extending either partially or entirely through the bone engaging portion 412, and may be further provided with transverse passages that communicate with the axial passage to define fenestration openings. Additionally, the cannulation and fenestration openings may be used to deliver material, such as, for example, bone cement through the bone engaging portion 412 and into areas of the bone axially or laterally adjacent the distal region 412a or laterally adjacent other portions of the bone engaging portion 412.

In the illustrated embodiment of the bone anchor 400, the screw head portion 414 is configured for engagement with a spinal plate (not shown). In one specific embodiment, the bone screw 400 includes an enlarged head 430 and a stem 432 extending from the enlarged head 430. In one embodiment, the enlarged head 430 includes an at least partially spherical or conical surface 434, and the stem 432 defines external threads 436. Additionally, the spinal plate includes one or more slots or openings configured to receive the threaded stem 432 of one or more of the bone anchors 400 therethrough, with the spinal plate secured to the bone anchors 400 via lock nuts (not shown) that are threaded onto the stem portions 432, thereby capturing the spinal plate between the enlarged heads 430 of the bone anchors 400 and the lock nuts. As should be appreciated, the design of the bone anchor 400 allows the spinal plate to be securely coupled to bone, while still maintaining a space or gap between the spinal plate and the outer surface of the bone. Additionally, a surface of the spinal plate adjacent the slots or openings may be provided with a number of spherical or conical shaped recesses for receiving the at least partially spherical or conical surface 434 of the enlarged head portions 430, thereby inhibiting unintended displacement of the bone anchors 400 along the length of the slot or opening, while allowing a degree of pivotal or rotational movement of the bone anchor 400 relative to the spinal plate prior to tightening of the lock nuts onto the threaded stem portions 432.

Further details regarding bone screws having configurations similar to the configuration of the bone anchor 400 are illustrated and described, for example, in U.S. Pat. No. 5,395,371 to Miller et al., the contents of which are hereby incorporated herein by reference. In still other embodiments of the invention, the screw head 414 may be configured without the threaded stem 432, with the spinal plate captured between the enlarged head portion 430 and an outer surface of the bone. One such bone screw embodiment is illustrated and described, for example, in U.S. Pat. No. 6,152,927 to Farris et al., the contents of which are hereby incorporated herein by reference. In a further embodiment of the invention, the bone anchor 400 may be configured for variable positioning along a length of a slot or opening in the spinal plate. One such embodiment is illustrated and described, for example, in U.S. Pat. No. 6,280,445 to Morrison et al., the contents of which are hereby incorporated herein by reference.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A bone anchor, comprising:
   a bone engaging element including external threads structured for engagement with bone and including:
      a first portion formed of a first material and defining at least a portion of said external threads;
      a second portion formed of a second material different from said first material and defining at least a portion of said external threads, said second portion extending at least partially along a length of said first portion and about a periphery of said first portion, said second portion of said bone engaging element positioned between said first portion and adjacent bone tissue when said bone engaging element is engaged with the bone to provide an interface with the adjacent bone tissue; and
   wherein said second material comprises a moldable material that is molded about said periphery of said first portion of said bone engaging element to form a unitary, single-piece structure, said at least a portion of said external threads defined by said second portion comprising molded external threads formed of said moldable material that are molded into said second portion of said bone engaging element; and
   wherein said first material exhibits a performance characteristic that differs from that of said second material; and
   wherein said bone engaging element extends along an axis and includes at least three distinct axial regions, said second portion of said bone engaging element extending along at least one of said axial regions and providing a buffer between said first portion of said bone engaging element and the adjacent bone tissue, said first portion of said bone engaging element extending along at least one of said axial regions and interfacing directly with adjacent bone tissue, and wherein said axial regions defined by said second portion of said bone engaging element formed of said second material are positioned in an alternating manner relative to said axial regions defined by said first portion of said bone engaging element formed of said first material; and
   wherein said at least a portion of said external threads defined by said first portion cooperates with said molded external threads defined by said second portion to form a substantially continuous threading extending along said at least three distinct axial regions of said bone engaging element; and
   an implant engaging element structured for coupling with an implant to anchor the implant to the bone.

2. The bone anchor of claim 1, wherein said performance characteristic comprises rigidity; and
   wherein said second portion of said bone engaging element is less rigid than said first portion of said bone engaging element.

3. The bone anchor of claim 1, wherein said performance characteristic comprises flexibility; and
   wherein said second portion of said bone engaging element is more flexible than said first portion of said bone engaging element.

4. The bone anchor of claim 1, wherein one of said first and second materials comprises a metallic material, and wherein the other of said first and second materials comprises a non-metallic material.

5. The bone anchor of claim 4, wherein said first material comprises a metallic material; and
   wherein said second material comprises a non-metallic material.

6. The bone anchor of claim 5, wherein said second material comprises a polymeric material.

7. The bone anchor of claim 5, wherein said second material comprises PEEK.

8. The bone anchor of claim 5, wherein said second material comprises a shape-memory polymer material.

9. The bone anchor of claim 1, wherein the bone anchor is configured to allow selective rotational or pivotal movement of said bone engaging element relative to said implant engaging element.

10. The bone anchor of claim 1, wherein said bone engaging element includes a distal region, a proximal region, and an intermediate region positioned between said distal and proximal regions;
    said second portion of said bone engaging element extending along said distal and proximal regions to provide said buffer between said first portion of said bone engaging element and the adjacent bone tissue; and
    said first portion of said bone engaging element extending along said intermediate region and interfacing directly with the adjacent bone tissue.

11. The bone anchor of claim 1, wherein said second material extends along an entire distal region of the bone engaging element including a distal end of said bone engaging element.

12. The bone anchor of claim 11, wherein said second material surrounds a distal-most end of said bone engaging element.

13. The bone anchor of claim 11, wherein said second material defines a tapered distal tip of said bone engaging element.

14. The bone anchor of claim 11, wherein said second material defines a rounded distal tip of said bone engaging element.

15. The bone anchor of claim 1, further comprising a head portion extending from said bone engaging element, said head portion including a pair of spaced apart arms defining a U-shaped passage having an open end.

16. The bone anchor of claim 15, further comprising an elongate spinal rod positionable within said U-shaped passage of said head portion.

17. The bone anchor of claim 15, wherein said pair of spaced apart arms each define internal threads configured for engagement with a set screw.

18. The bone anchor of claim 1, wherein said substantially continuous threading extends along substantially an entire length of said bone engaging element.

19. A bone anchor, comprising:
a shank element having a length and defining external threads configured for engagement within an opening in bone, said shank element including:
a core portion formed of a first material; and
a bone interface portion formed of a second material less rigid than said first material, wherein said second material comprises a moldable material and wherein said bone interface portion is molded about said core portion to form a unitary, single-piece structure, said bone interface portion extending along a length of said core portion and about a periphery of said core portion, said bone interface portion defining at least a portion of said external threads of said shank element, wherein said at least a portion of said external threads comprise molded external threads that are molded into said bone interface portion;
wherein said core portion defines at least a portion of said external threads of said shank; and
wherein said at least a portion of said external threads defined by said core portion cooperates with said at least a portion of said external threads defined by said bone interface portion to form a substantially continuous threading extending along said shank element; and
an implant engaging element structured for coupling with an implant to anchor the implant to the bone.

20. The bone anchor of claim 19, wherein said shank element extends along an axis and includes at least three distinct axial regions, said bone interface portion of said shank element extending along at least one of said axial regions and providing a buffer between said core portion of said shank element and adjacent bone tissue, said core portion of said shank element extending along at least one of said axial regions and interfacing directly with adjacent bone tissue, and wherein said axial regions defined by said bone interface portion of said shank element are positioned in an alternating manner relative to said axial regions defined by said core portion of said shank element.

21. The bone anchor of claim 19, wherein said moldable material comprises a polymeric material.

22. The bone anchor of claim 19, wherein said core portion is formed of a metallic material; and
wherein said bone interface portion is formed of a non-metallic material.

23. The bone anchor of claim 22, wherein said non-metallic material comprises a polymeric material.

24. The bone anchor of claim 19, wherein said substantially continuous threading extends along substantially an entire length of said shank element.

25. A method of forming a bone anchor, comprising:
providing a bone engaging element for anchoring to bone and an implant engaging element for coupling with an implant;
forming a first portion of the bone engaging element from a first material;
forming a second portion of the bone engaging element from a second material different from the first material, the forming of the second portion of the bone engaging element comprising molding the second material about a periphery of the first portion and along a length of the first portion to form a unitary, single-piece structure and to provide an interface between the first portion and adjacent bone when the bone engaging element is engaged with the bone; and
forming external threads along a length of the first portion of the bone engaging element by a machining process and forming external threads along a length of the second portion of the bone engaging element by a molding process, the external threads of the first portion cooperating with the external threads of the second portion to form a substantially continuous thread extending along the bone engaging element; and
wherein the forming of the external threads along the second portion of the bone engaging element is accomplished during the molding.

26. The method of claim 25, wherein the forming of the second portion of the bone engaging element comprises molding the second portion entirely about the periphery of the first portion.

27. The method of claim 25, wherein the second portion of the bone engaging element extends along substantially an entire length of the first portion of the bone engaging element.

28. The method of claim 25, wherein the bone engaging element includes a distal region and a proximal region, the second portion of the bone engaging element extending along the proximal region to provide the interface between the first portion and the adjacent bone, the first portion of the bone engaging element interfacing directly with adjacent bone along the distal region of the bone engaging element.

29. The method of claim 28, further comprising providing the first portion of the bone engaging element with cutting features along the distal region of the bone engaging element to provide the bone anchor with at least one of a self-cutting capability and a self-tapping capability.

30. The method of claim 25, wherein the bone engaging element includes a distal region and a proximal region, the second portion of the bone engaging element extending along the distal region to provide the interface between the first portion and the adjacent bone, the first portion of the bone engaging element interfacing directly with adjacent bone along the proximal region of the bone engaging element.

31. The method of claim 25, wherein the first portion of the bone engaging element exhibits a first level of rigidity, the second portion of the bone engaging element exhibiting a second level of rigidity less than the first level of rigidity.

32. The method of claim 25, wherein the molding comprises injection molding.

33. The method of claim 32, wherein the injection molding comprises plastic injection molding.

34. The method of claim 32, wherein the injection molding comprises metal injection molding.

35. The method of claim 25, wherein the molding comprises overmolding.

36. The method of claim 25, wherein one of said first and second materials comprises a metallic material, and wherein the other of the first and second materials comprises a non-metallic material.

37. The method of claim 36, wherein the first material comprises a metallic material, and wherein the second material comprises a polymeric material.

38. The method of claim 25, wherein the substantially continuous thread extends along substantially an entire length of the bone engaging element.

* * * * *